(12) United States Patent
Mallat et al.

(10) Patent No.: US 9,573,997 B2
(45) Date of Patent: Feb. 21, 2017

(54) METHOD FOR USE IN THE TREATMENT OF ANEURYSM

(71) Applicants: INSERM (Institut National de la Sante et de la Recherche Medicale), Psris (FR); Universite Paris Descartes, Paris (FR)

(72) Inventors: Ziad Mallat, Paris (FR); Soraya Taleb, Paris (FR); Alain Tedgui, Paris (FR)

(73) Assignees: INSERM (Institut National de la Sante et de la Recherche Medicale), Paris (FR); Universite Paris Descartes, Paris (FR)

( * ) Notice: Subject to any disclaimer, the term of this patent is extended or adjusted under 35 U.S.C. 154(b) by 231 days.

(21) Appl. No.: 14/386,250

(22) PCT Filed: Mar. 15, 2013

(86) PCT No.: PCT/EP2013/055385
§ 371 (c)(1),
(2) Date: Sep. 18, 2014

(87) PCT Pub. No.: WO2013/139701
PCT Pub. Date: Sep. 26, 2013

(65) Prior Publication Data
US 2015/0050290 A1 Feb. 19, 2015

(30) Foreign Application Priority Data
Mar. 19, 2012 (EP) ..................................... 12305323

(51) Int. Cl.
*A61K 38/20* (2006.01)
*A61P 9/00* (2006.01)
*C07K 16/24* (2006.01)
*C07K 14/545* (2006.01)
*A61K 39/00* (2006.01)

(52) U.S. Cl.
CPC ......... *C07K 16/245* (2013.01); *A61K 38/2006* (2013.01); *A61K 2039/505* (2013.01); *C07K 2317/76* (2013.01)

(58) Field of Classification Search
None
See application file for complete search history.

(56) References Cited

U.S. PATENT DOCUMENTS 6,437,216 B1 * 8/2002 Duff et al. ...................... 800/21
2011/0189172 A1 * 8/2011 Solinger et al. ........... 424/133.1

FOREIGN PATENT DOCUMENTS

WO 2013049278 4/2013

OTHER PUBLICATIONS

Shayakhmetov et al, 2005. J Immunol. 174: 7310-7319.*
Moriwaki Takuya et al., "Impaired progression of cereberal aneurysms in interleukin-1 beta-deficient mice", Stroke, vol. 37, No. 3, Mar. 2006 p. 900-905.
Lee Youngho et al., "Interleukin-1 [beta] is crucial for the induction of coronary artery inflammation in a mouse model of Kawasaki disease", Lippincot Williams and Wilkins, vol. 125, No. 12, Feb. 23, 2012, p. 1542-1550.
Lei Zhang et al., "Overexpression of interleukin-1 and interferon- in type 1 thoracic aortic dissections and ascending thoracic aortic aneurysms: possible correlation with matrix metalloproteinase-9 expression and apoptosis of aortic media cells", European Journal of Cardio-Thoracic Surgery, vol. 40, No. 1, Sep. 5, 2010, p. 17-22.
Wang Yu et al., "TGF-beta activity protects against inflammatory aortic aneurysm progression and complications in angiotensin II-infused mice", Journal of Clinical Investigation, vol. 120, No. 2, p. 422-432.

\* cited by examiner

*Primary Examiner* — Zachary Howard
(74) *Attorney, Agent, or Firm* — Whitham, Curtis & Cook, P.C.

(57) ABSTRACT

The present invention relates to a compound which is an antagonist of IL-1 beta or an inhibitor of IL-1 beta expression for use in the treatment or the prevention of aneurysm. In another embodiment, the invention relates to a pharmaceutical composition for use in the treatment or the prevention of aneurysm comprising an antagonist of IL-1 beta or an inhibitor of IL-1 beta expression.

1 Claim, 4 Drawing Sheets

METHOD FOR USE IN THE TREATMENT OF ANEURYSM

FIELD OF THE INVENTION

Figure 1:
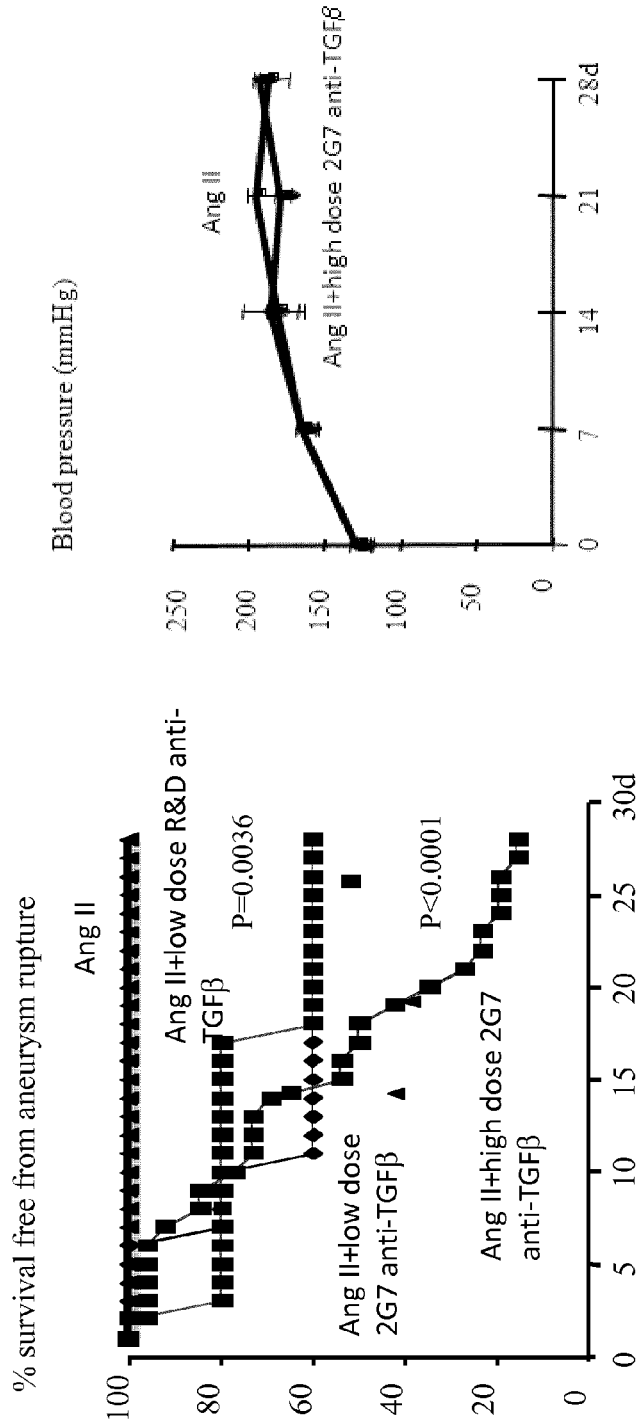

The present invention relates to a compound which is an antagonist of IL-1 beta or an inhibitor of IL-1 beta expression for use in the treatment or the prevention of aneurysm.

In another embodiment, the invention relates to a pharmaceutical composition for use in the treatment or the prevention of aneurysm comprising an antagonist of IL-1 beta or an inhibitor of IL-1 beta expression.

BACKGROUND OF THE INVENTION

Aneurysm is a localized dilation (balloon-like bulge) of a blood vessel caused by disease or weakening of the vessel wall. Aneurysms most commonly occur in arteries at the base of the brain (the circle of Willis) and in the aorta (the main artery coming out of the heart), a so-called aortic aneurysm. The bulge in a blood vessel can burst and lead to death at any time. The larger an aneurysm becomes, the more likely it is to burst and since aneurysms naturally grow, given enough time they will inevitably reach the bursting point if undetected.

Given the severe consequences of an aneurysm, screening is now commonly performed in order to early detect the presence of an aneurysm. In case of an aortic aneurysm the blood-filled dilation is commonly located in the abdomen in the infra-renal aorta close to the iliac bifurcation extending to the legs. At this location the aorta is typically about 2.5 centimeters wide, which can be measured for example using ultra-sonic or X-ray based measuring devices.

Existing treatment when detecting an aortic aneurysm includes implantation of a grafted around the vessel using open surgery. An alternative surgical procedure is to implant a tube from the groin and guide a stentgraft via arteria femoralis into position where the blood flow can by-pass the aortic aneurysm via the tube. The latter treatment has the drawback of increased rates of re-intervention.

Thus, there exists a need for alternative treatment of aneurysm that does not involve surgery.

SUMMARY OF THE INVENTION

Working on an in-vivo model of aneurysm, the inventors discovered that the KO of IL-1 beta reduces fatal aortic rupture and increases the survival of mice.

Thus, the invention relates to a compound which is an antagonist of IL-1 beta or an inhibitor of IL-1 beta expression for use in the treatment or the prevention of aneurysm.

In another embodiment, the invention relates to a pharmaceutical composition for use in the treatment or the prevention of aneurysm comprising an antagonist of IL-1 beta or an inhibitor of IL-1 beta expression.

DETAILED DESCRIPTION OF THE INVENTION

A first object of the invention relates to a compound which is an antagonist of IL-1 beta or an inhibitor of the IL-1 beta expression for use in the treatment or the prevention of aneurysm.

Interleukin 1 beta (IL-1 beta) is well known. IL-1 beta is a member of the interleukin 1 cytokine family. This cytokine is produced as a proprotein, which is proteolytically processed to its active form by caspase 1 (CASP1/ICE). This cytokine is an important mediator of the inflammatory response, and is involved in a variety of cellular activities, including cell proliferation, differentiation, and apoptosis.

As used herein, the term "treating" or "treatment", denotes reversing, alleviating, inhibiting the progress of, or preventing the disorder or condition to which such term applies, or reversing, alleviating, inhibiting the progress of, or preventing one or more symptoms of the disorder or condition to which such term applies.

As used herein the term "antagonist of IL-1 beta" refers to any compound that inhibits the activity of IL-1 beta. Typically, said antagonist may inhibit or not the activity of IL1 alpha. However in a particular embodiment said antagonist inhibits specifically the activity of IL-1 beta over IL-1 alpha.

In a preferred embodiment, the aneurysm is an aortic, a peripheral or an intracranial aneurysm.

In one embodiment, said IL-1 beta antagonist may be a small organic molecule (natural or not). The term "small organic molecule" refers to a molecule (natural or not) of a size comparable to those organic molecules generally used in pharmaceuticals. The term excludes biological macromolecules (e. g., proteins, nucleic acids, etc.). Preferred small organic molecules range in size up to about 10000 Da, more preferably up to 5000 Da, more preferably up to 2000 Da and most preferably up to about 1000 Da.

In another embodiment, IL-1 beta antagonist of the invention may be an anti-IL-1 beta antibody which neutralizes IL-1 beta or an anti-IL-1 beta fragment thereof which neutralizes IL-1 beta.

Antibodies directed against IL-1 beta can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against IL-1 beta can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see e.g., U.S. Pat. No. 4,946,778) can be adapted to produce anti-IL-1 beta single chain antibodies. IL-1 beta antagonists useful in practicing the present invention also include anti-IL-1 beta antibody fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to IL-1 beta.

Humanized anti-IL-1 beta antibodies and antibody fragments therefrom can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

Then, for this invention, neutralizing antibodies of IL-1 beta are selected.

In a particular embodiment, the antibody according to the invention may be the canakinumab (see for example Church L D et al 2010).

In a particular embodiment, the antibody according to the invention may be an antibody according to the patent application US2009226461.

In a particular embodiment, the antibody according to the invention may be the ACZ885 antibody (see for example the patent application WO2010066762).

In a particular embodiment, the antibody according to the invention may be an antibody according to the patent application WO0153353.

In a particular embodiment, the antibody according to the invention may be the Hu007 antibody (see for example the patent application WO03073982).

In a particular embodiment, the antibody according to the invention may be an antibody according to the patent application U.S. Pat. No. 5,348,858.

In a particular embodiment, the antibody according to the invention may be an antibody according to the patent application EP0364778.

In a particular embodiment, the antibody according to the invention may be an antibody according to the patent application U.S. Pat. No. 7,566,772.

In a particular embodiment, the antibody according to the invention may be an antibody according to the patent application U.S. Pat. No. 7,714,120.

In a particular embodiment, the antibody according to the invention may be an antibody according to the patent application US20110182894.

In a particular embodiment, the antibody according to the invention may be an antibody according to the patent application U.S. Pat. No. 4,935,343.

In a particular embodiment, the antibody according to the invention may be an antibody according to the patent application US20090226461.

In one embodiment, the invention relates to a compound which is an antagonist of IL-1 beta or an inhibitor of the IL-1 beta expression for use in the treatment or the prevention of aneurysm 1 wherein the antagonist is an anti-IL-1 beta antibody.

In still another embodiment, IL-1 beta antagonists may be selected from aptamers. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996).

The neutralizing aptamers of IL-1 beta may be easily selected by the skilled man in the art.

In a preferred embodiment, the compound according to the invention is an inhibitor of the IL-1 beta expression.

Small inhibitory RNAs (siRNAs) can also function as inhibitors of IL-1 beta gene expression for use in the present invention. IL-1 beta gene expression can be reduced by contacting a subject or cell with a small double stranded RNA (dsRNA), or a vector or construct causing the production of a small double stranded RNA, such that IL-1 beta gene expression is specifically inhibited (i.e. RNA interference or RNAi). Methods for selecting an appropriate dsRNA or dsRNA-encoding vector are well known in the art for genes whose sequence is known (e.g. see for example Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes can also function as inhibitors of IL-1 beta gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of IL-1 beta mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of IL-1 beta gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life.

Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing IL-1 beta. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, 1990 and in Murry, 1991).

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, eye, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In a preferred embodiment, the antisense oligonucleotide, siRNA, shRNA or ribozyme nucleic acid sequence is under the control of a heterologous regulatory region, e.g., a heterologous promoter. The promoter may be specific for Muller glial cells, microglia cells, endothelial cells, pericyte cells and astrocytes. For example, a specific expression in Muller glial cells may be obtained through the promoter of the glutamine synthetase gene is suitable. The promoter can also be, e.g., a viral promoter, such as CMV promoter or any synthetic promoters.

In order to test the functionality of putative IL-1 beta compounds on aneurysm, an in vitro/in vivo test is necessary. For that purpose, a model of aneurysm is highly relevant.

Another object of the invention relates to a method for treating or preventing aneurysm comprising administering to a subject in need thereof a therapeutically effective amount of compound which is an antagonist of IL-1 beta or an inhibitor of the IL-1 beta expression as described above.

In one aspect, the invention relates to a method for treating or preventing aneurysm comprising administering to a subject in need thereof a therapeutically effective amount of an IL-1 beta antagonist as above described.

In a preferred embodiment, the antagonist is an anti-IL-1 beta antibody

Compounds of the invention may be administered in the form of a pharmaceutical composition, as defined below.

Thus, a further object of the invention relates to pharmaceutical compositions comprising an antagonist of IL-1 beta or an inhibitor of IL-1 beta expression for the prevention or treatment of aneurysm.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The antagonist of IL-1 beta or the inhibitor of IL-1 beta expression of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The antagonist of IL-1 beta or the inhibitor of IL-1 beta expression of the invention may be formulated within a therapeutic mixture to comprise about 0.0001 to 1.0 milligrams, or about 0.001 to 0.1 milligrams, or about 0.1 to 1.0 or about 1.0 to 10 milligrams, or about 10 to 100 milligrams, or about 100 to 200 milligrams, or even about 200 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

The invention will be further illustrated by the following figures and examples. However, these examples and figures should not be interpreted in any way as limiting the scope of the present invention.

FIGURES

FIG. 1: Neutralization of TGF-β activity induces a highly permissive state to Ang II-induced AAA formation and complications. AngII was infused continuously via osmotic pumps at a rate of 1 µg/Kg/min. Anti-TGF beta antibody was administered as described in Wang Y et al., J Clin Invest 2010.

Figure 2:
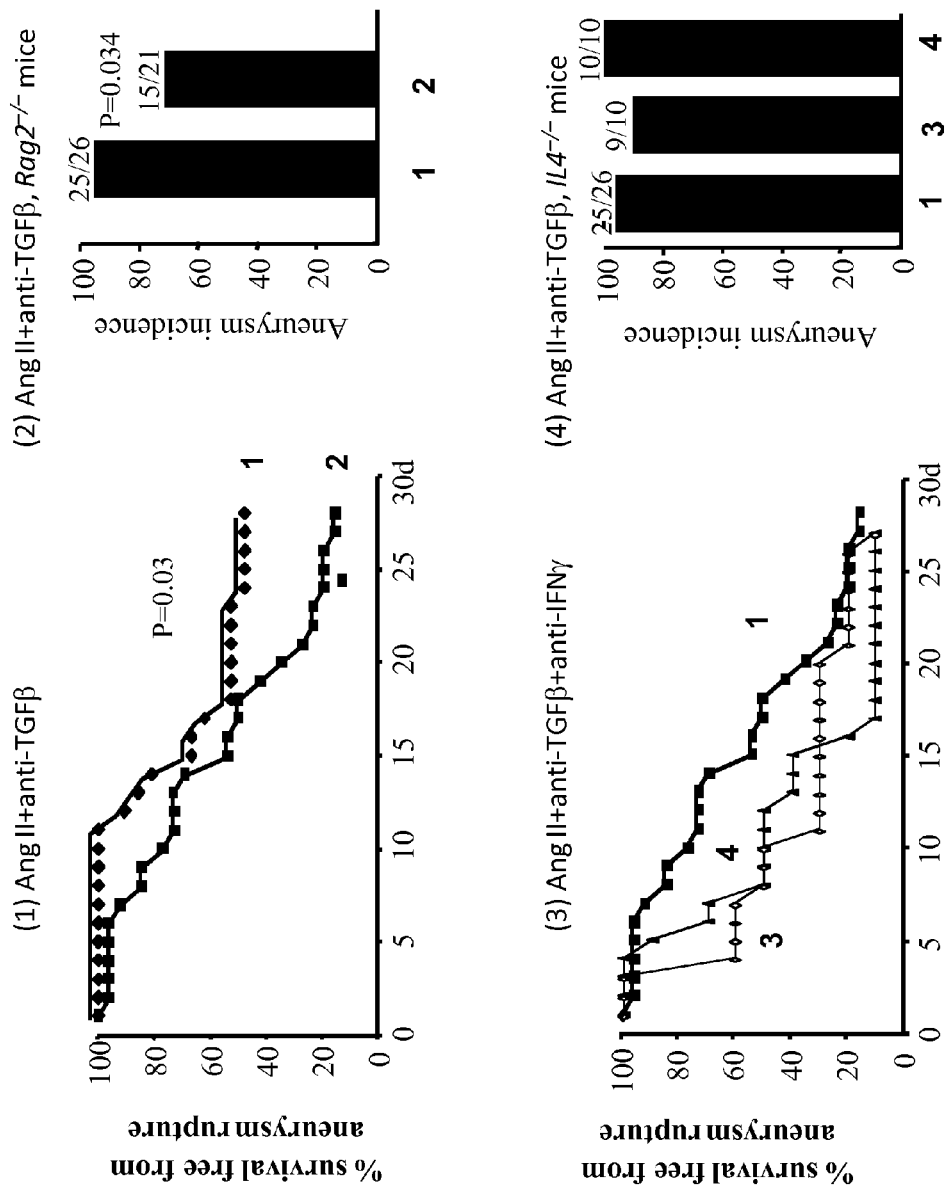

FIG. 2: AAA is slightly reduced in Rag2 KO (1 and 2) mice and is not prevented by inhibition of IFN-γ, IL-4 signaling (3 and 4). AngII was infused continuously via osmotic pumps at a rate of 1 μg/Kg/min. Anti-TGF beta and anti-IFN-gamma antibodies were administered as described in Wang Y et al., J Clin Invest 2010.

Figure 3:
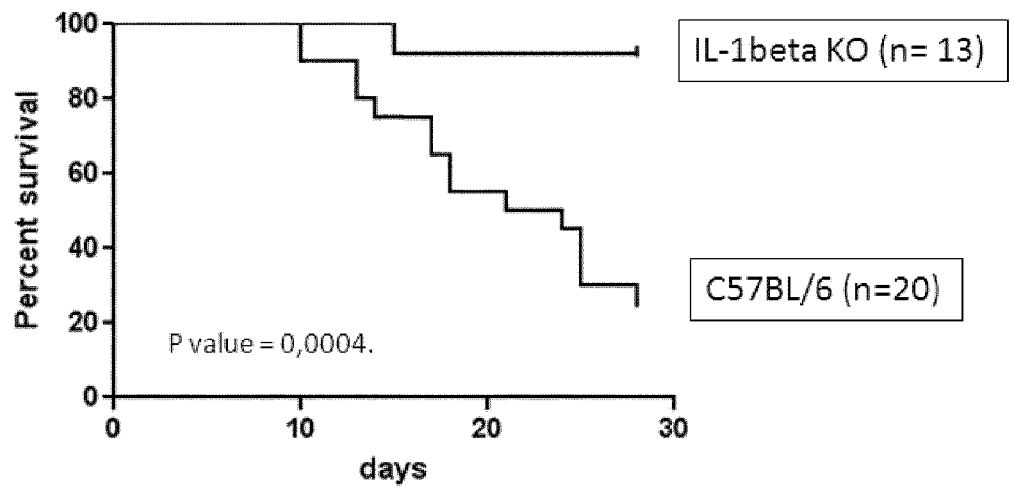

FIG. 3: IL-1 beta deficiency protects from fatal aneurysm rupture. AngII was infused continuously via osmotic pumps at a rate of 1 μg/Kg/min. Anti-TGF beta antibody was administered as described in Wang Y et al., J Clin Invest 2010.

Figure 4:
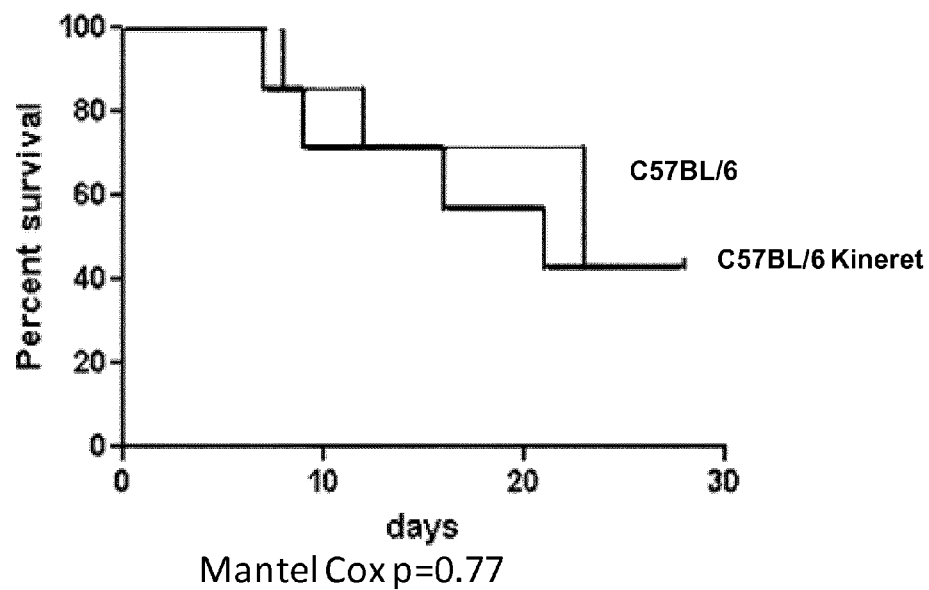

FIG. 4: Treatment with Anakinra (Kineret) does not protect from fatal aneurysm rupture. AngII was infused continuously via osmotic pumps at a rate of 1 μg/Kg/min. Anti-TGF beta antibody was administered as described in Wang Y et al., J Clin Invest 2010. Kineret was administered at 100 mg/kg, 3 times per week.

Figure 5:
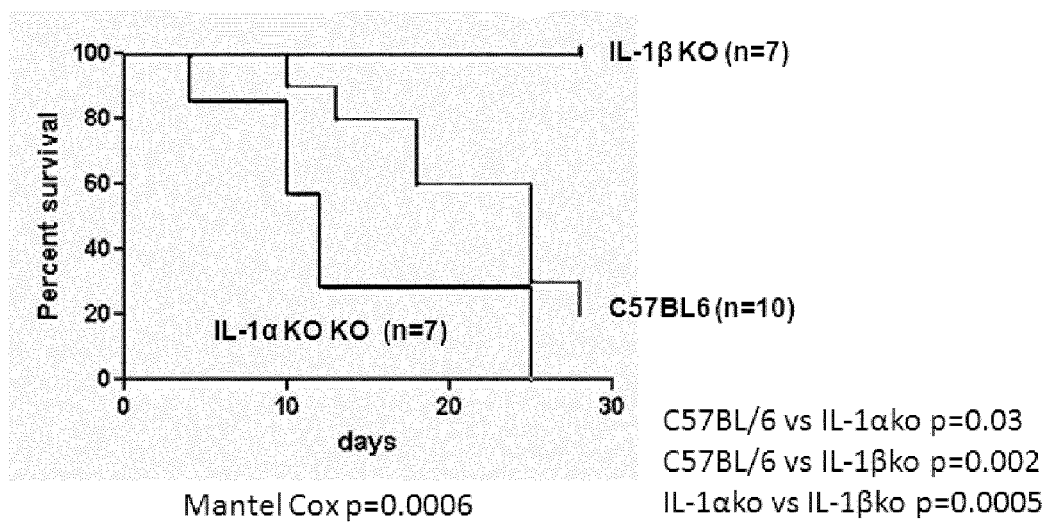

FIG. 5: Contrary to IL-beta deficiency, IL-1 alpha deficiency does not protect from fatal aneurysm rupture. AngII was infused continuously via osmotic pumps at a rate of 1 μg/Kg/min. Anti-TGF beta antibody was administered as described in Wang Y et al., J Clin Invest 2010.

EXAMPLE

Material & Methods

We used male mice between 8 and 12 weeks of age. C57BL/6J IL-1$\beta^{-/-}$ and IL-1$\alpha^{-/-}$ mice were used. C57BL/6J Rag2$^{-/-}$ mice were purchased from Centre de Cryopréservation, Distribution, Typage et Archivage animal or were provided by Olivier Lantz, Institut Curie, Paris, France. C57BL/6J Il4$^{-/-}$ mice were purchased from The Jackson Laboratory. Neutralizing purified monoclonal rat IgG1 anti-IFN-γ antibody (clone XMG.1) was produced by L. Rénia. Mouse anti-human TGF-β (β1, β2, and β3) (clone 2G7) was produced by BIOTEM. Polyclonal rabbit anti-TGF-β was from R&D Systems (AB-100-NA, lot number EO16). Kineret (anakinra) is a recombinant, nonglycosylated form of the human interleukin-1 receptor antagonist (IL-1Ra). Kineret was obtained from Amgen and was used at 100 mg/kg, 3 injections per week. Angiotensin II was purchased from Sigma-Aldrich, and ALZET osmotic pumps were from Charles River Laboratories.

The Mouse Model of Ang II-Induced Aortic Aneurysm.

The mouse model of Ang II-induced aneurysm formation has been previously described (Wang Y J Clin Invest 2010). Ang II was infused via subcutaneous osmotic pumps at 1,000 ng/kg/min for a maximum of 28 days. Kaplan-Meier survival curves were constructed and analyzed using log-rank (Mantel-Cox) test. P values of less than 0.05 were considered significant.

Results

Results are illustrated in FIGS. 1-5. Neutralization of TGF-β activity induces a highly permissive state to Ang II-induced AAA formation and complications (FIG. 1). AAA is not prevented by inhibition of IFN-γ, IL-4 signalling (FIG. 2). IL-1 beta deficiency protects from fatal aneurysm rupture (FIG. 3). Treatment with Anakinra (Kineret) does not protect from fatal aneurysm rupture (FIG. 4). Contrary to IL-beta deficiency, IL-1 alpha deficiency does not protect from fatal aneurysm rupture (FIG. 5).

REFERENCES

Throughout this application, various references describe the state of the art to which this invention pertains. The disclosures of these references are hereby incorporated by reference into the present disclosure.

Church L D, McDermott M F. Canakinumab: a human anti-IL-1β monoclonal antibody for the treatment of cryopyrin-associated periodic syndromes. Expert Rev Clin Immunol. 2010 November; 6(6):831-41.

Solignac M. Mechanisms of action of diacerein, the first inhibitor of interleukin-1 in osteoarthritis. Presse Med. 2004 May 22; 33(9 Pt 2):S10-2.

The invention claimed is:
1. A method of treating an abdominal aortic aneurysm in a subject in need thereof, consisting essentially of
administering to said subject a therapeutically effective amount of a compound which is an antagonist of IL-1 beta, wherein the antagonist is an anti-IL-1 beta antibody specific for IL-1 beta.

* * * * *